United States Patent

Rosing et al.

[11] Patent Number: 6,074,683
[45] Date of Patent: Jun. 13, 2000

[54] PROCESS FOR THE PREPARATION OF A SAVORY FLAVOR

[75] Inventors: Egge Aart Rosing, Schiedam; Hessel Turksma, Delft, both of Netherlands

[73] Assignee: Lipton, Inc., Englewood Cliffs, N.J.

[21] Appl. No.: 08/779,691

[22] Filed: Jan. 7, 1997

[30] Foreign Application Priority Data

Jan. 17, 1996 [EP] European Pat. Off. .............. 96300328

[51] Int. Cl.⁷ ....................................................... A23L 1/22
[52] U.S. Cl. ........................... 426/533; 426/534; 426/536; 426/538; 426/650
[58] Field of Search ..................... 426/533, 535, 426/534, 536, 538, 650

[56] References Cited

U.S. PATENT DOCUMENTS

| | | | |
|---|---|---|---|
| 4,055,578 | 10/1977 | Evers | 549/475 |
| 4,080,367 | 3/1978 | van den Ouweland et al. | 549/477 |
| 4,096,158 | 6/1978 | Evers et al. | 426/535 |

FOREIGN PATENT DOCUMENTS

| | | |
|---|---|---|
| 340748 | 12/1977 | Austria . |
| 571 031 | 11/1993 | European Pat. Off. . |
| 858333 | 1/1961 | United Kingdom . |
| 1256462 | 12/1971 | United Kingdom . |
| 1283912 | 8/1972 | United Kingdom . |
| 1283913 | 8/1972 | United Kingdom . |
| 1302525 | 1/1973 | United Kingdom . |
| 1434194 | 5/1976 | United Kingdom . |

OTHER PUBLICATIONS

Artander, S., Perfume and Flavor Chemicals, vol. I, No. 1416, 1417, 1969, Montclair, NJ.

*Primary Examiner*—Leslie Wong
*Attorney, Agent, or Firm*—James J. Farrell

[57] ABSTRACT

A process for preparing a savory flavor, the process comprising reacting a compound of general formula X with hydrogen sulphide and/or cystein, wherein X is:

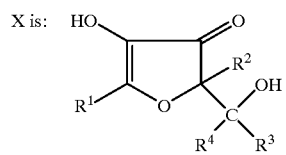

in which $R^1$ represents an alkyl group having 1 or 2 carbon atoms or hydrogen, $R^2$ represents an alkyl group having from 1 to 4 carbon atoms or hydrogen, $R^3$ represents an alkyl group having from 1 to 5 carbon atoms or hydrogen and $R^4$ represents hydrogen or an organic radical consisting of from 1 to 6 carbon atoms, hydrogen and from 0 to 2 oxygen atoms. X is preferably 4-hydroxy-2,5-dimethyl-2-(2-hydroxy-3-oxo-2-butyl)-3(2H)-furanone, and is formed from the reaction of 4-hydroxy-2,5-dimethyl-3(2H)-furanone and diacetyl. 2,5-dimethyl-4-mercapto-3(2H)-furanone is a flavor compound obtainable by this process.

10 Claims, 4 Drawing Sheets

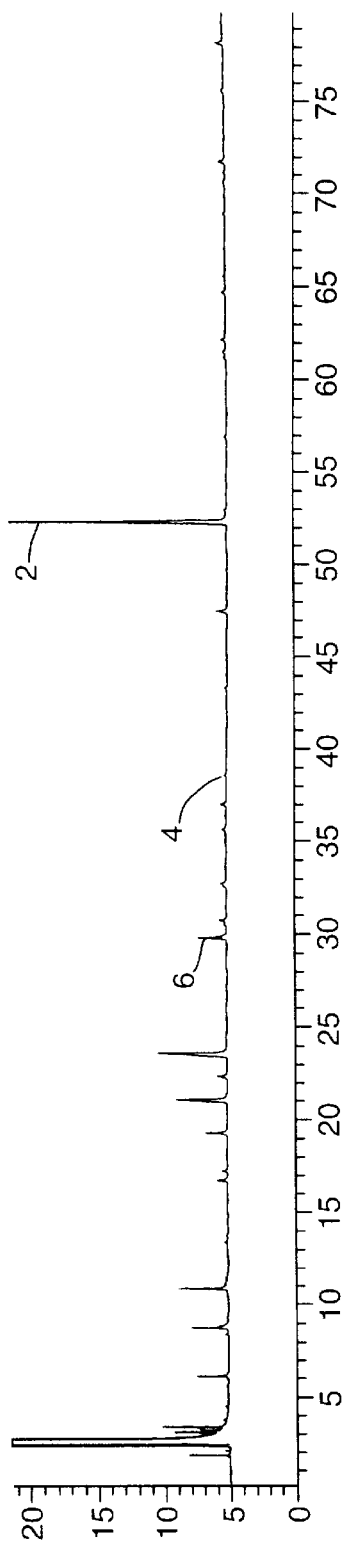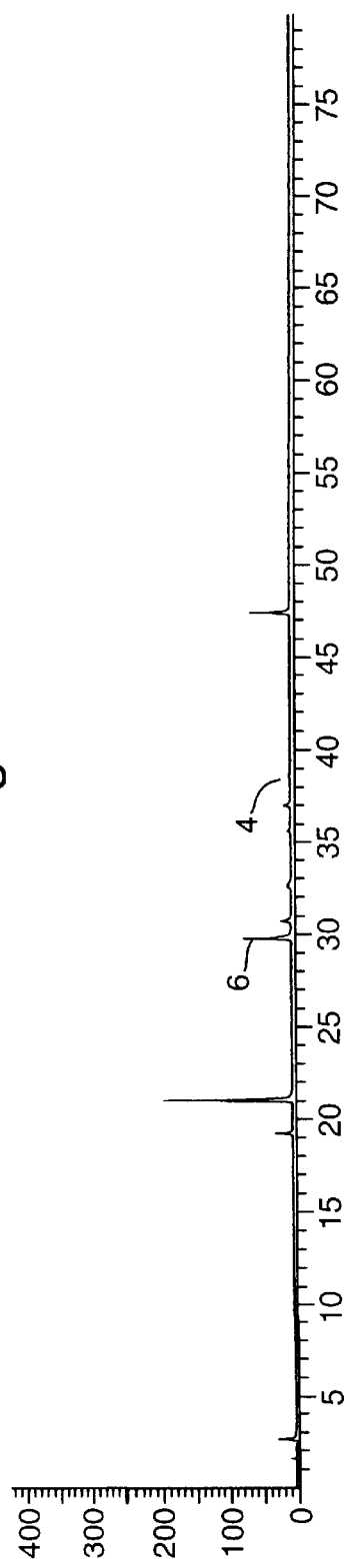

PROCESS FOR THE PREPARATION OF A SAVORY FLAVOR

FIELD OF THE INVENTION

The present invention relates to savoury flavours, processes for their preparation, and their use in the flavouring of foodstuffs. In particular, this invention is concerned with savoury flavours which resemble that of roast, fried or boiled meat.

Flavouring is understood to be the incorporation of compounds having flavouring characteristics per se, as well as the incorporation of precursor compounds which may not themselves possess flavouring characteristics, but which during the preparation of foodstuffs release or are converted into products having flavouring characteristics.

BACKGROUND ART

Processes for the preparation of savoury flavours are known in the art:

GB 1256462 discloses meat-like flavouring compositions and methods of preparing them. The flavouring compositions comprise organic oxygen-containing heterocyclics wherein the second carbon atom from the oxygen atom contains a sulphur substituent.

GB 1434194 describes the preparation of addition compounds from the reaction of mono- or dialkylfurenidones (e.g. 2,5-dimethyl-4-hydroxy-3-(2H)-furanone) with carbonyl compounds, such as ketones. These addition compounds are stable upon storage and, since they are precursors of furenidones, they can be incorporated into foodstuffs where, upon heating of the foodstuffs, they revert to free furenidones, which have flavouring properties.

GB 1283912 and GB 1283913 describe processes for preparing meat-like flavouring substances; the processes comprise reacting certain heterocyclic ketones, such as 4-hydroxy-2,5-dimethyl-2,3-dihydrofuran-3-one or 4-hydroxy-5-methyl-2,3-dihydrofuran-3-one, with hydrogen sulphide or other sulphur-containing compounds (e.g. cysteine) in the presence of water. Although, these processes permit the synthesis of interesting savoury mixtures, they are not very specific, so do not form high yields of key meat flavours (eg. see Examples B1 and B2 of GB 1283912).

EP-A-571031 discloses a process for the preparation of a savoury flavour which comprises reacting mono- and/or di-methyl-3(2H)-furanone, or precursors thereof, with cystein and/or hydrogen sulphide. No hydroxy group is carried in the four position. A suitable precursor is 2,5-dimethyl-2-(2-hydroxy-3-oxo-2-butyl)-3(2H)-furanone, which is a diacetyl oligomer. The process results in high yields of certain key compounds, namely methyl-substituted furanthiols, their disulphides and methyl-substituted furanthiolacetates. The reaction of 2,5-dimethyl-2-(2-hydroxy-3-oxo-2-butyl)-3(2H)-furanone with $H_2S$ and cystein results in a 32% yield of 2,5-dimethyl-furan-3-thiol (see example 8 of EP 571031 and comparative example D of the present application): FIG. 2 of the present application is a chromatograph of the resultant savoury flavour mixture showing that this key sulphur-containing flavour compound (peak 8) is present.

The present invention seeks to provide a new process for preparing a savoury flavour mixture, the process preferably providing a good yield of a number of key flavour compounds.

SUMMARY OF THE INVENTION

According to the present invention there is provided a process for the preparation of a savoury flavour, the process comprising reacting a compound of general formula X with hydrogen sulphide and/or cystein, wherein X is:

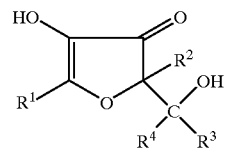

in which $R^1$ represents an alkyl group having 1 or 2 carbon atoms or hydrogen, $R^2$ represents an alkyl group having from 1 to 4 carbon atoms or hydrogen, $R^3$ represents an alkyl group having from 1 to 5 carbon atoms or hydrogen and $R^4$ represents hydrogen or an organic radical consisting of from 1 to 6 carbon atoms, hydrogen and from 0 to 2 oxygen atoms.

Compound X occurs in two stereo-isometric forms; both forms are suitable as flavour precursors for the purpose of this invention.

Preferably, compound X is formed by reacting a compound of general formula Y with a compound of general formula Z where Y is:

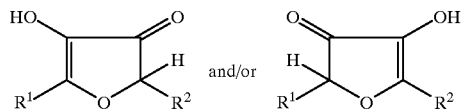

and Z is:

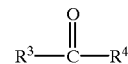

Preferred examples of compound Y are 4-hydroxy-2,5-dimethyl-3(2H)-furanone, 4-hydroxy-2-methyl-3(2H)-furanone, 4-hydroxy-5-methyl-3(2H)-furanone, 3-hydroxy-2,5-dimethyl-4(5H)-furanone, 3-hydroxy-2-methyl-4(5H)-furanone, and 3-hydroxy-5-methyl-4(5H)-furanone.

Preferred examples of compound Z are diacetyl, butanal, hexanal, pyruvic aldehyde, pyruvic acid, acetoin, acetol, ethylene glycol aldehyde, pentanedione and glyceraldehyde.

In a particularly preferred embodiment, Y is 4-hydroxy-2,5-dimethyl-3(2H)-furanone, i.e.

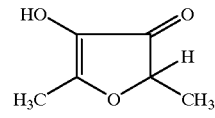

Z is diacetyl, i.e.

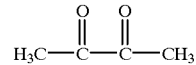

and the adduct formed from the reaction of Y and Z is 4-hydroxy-2,5-dimethyl-2-(2-hydroxy-3-oxo-2-butyl)-3 (2H)-furanone, which is X.

Preferably, compound X is reacted with both cystein and hydrogen sulphide.

Hydrogen sulphide may be generated by a hydrogen sulphide donor. Suitable hydrogen sulphide donors can be any organic or inorganic compound which is capable of generating hydrogen sulphide either in the gaseous or nascent form under reaction conditions. Suitable examples are: peptides containing cystein such as glutathione, cystine, mercaptoaceetamide, thioaceetamide, or salts thereof, for example: potassium or sodium salts, hydrochlorides, esters or simple derivatives of other simple derivatives of the sulphur-containing compound. Suitable inorganic sulphur-containing compounds are sulphides or hydrosulphides of alkali metals, alkaline earth metals or ammonia, such as sodium sulphide, potassium sulphide, ammonium sulphide, calcium sulphide, and the corresponding hydrosulphides. Also other metal sulphides, for example ferrous sulphide may be used. The use of hydrogen sulphide donors obtained from animal, vegetable or microbiological sources is preferred.

In another preferred embodiment of the invention the molar ratio of compound X: cystein: hydrogen sulphide available for reaction is within the range 1:5–15:0–10, preferably within the range 1:7–9:3–5.

A flavour compound obtainable by this process is 2,5-dimethyl-4-mercapto-3(2H)-furanone.

In order to obtain higher yields of flavour compounds the process according to the present invention is preferably carried out in a medium comprising a polar solvent, preferably an organic polar solvent. In an aqueous medium, it is usual to obtain lower yields than in a polar organic medium. As the presence of water may negatively affect the yield, the present reaction medium contains preferably less than 20%, more preferably less than 5%, of water. Many organic polar solvents are suitable in principle, but preferred are those whose presence is allowed in foods by the various food regulations, such as propylene glycol or glycerol. Commercial grades thereof often contain about 1% of water and can be used as such.

Preferably the process is carried out at a pH below 7, preferably from 2 to 6. The pH of the reaction mixture is conveniently determined after adding 90% (w.w.) of water to 10% of the organic polar medium. Usually the pH of the reaction medium increases somewhat as the reaction proceeds.

The process according to the present invention is preferably carried out at a temperature between 60 and 180° C. for 0.5 to 4 hours, preferably between 90 and 120° C. for 1 to 3 hours. The use of higher reaction temperatures tends to lead to savoury flavours with a roast meat note, whereas those prepared at lower temperatures tend to lead to a more sweet meaty note. Lower temperatures (eg 100° C.) are preferred.

The process according to the present invention is preferably carried out in an autoclave at superatmospheric pressure, preferably from 100 to 2,500 KPa, optionally in the presence of air. The use of an autoclave is convenient, especially when using hydrogen sulphide, and it may be desirable to effect some air oxidation so as to form the corresponding disulphides. Carrying out the process in the presence of oxygen (ie. in a system open to the atmosphere) results in aroma compounds which may be different to those formed by carrying out the process in the absence of air (eg. in a system closed to the atmosphere ie. in an autoclave).

In another embodiment of the invention, there is provided a flavour precursor mixture, generating a savoury flavour upon heating, and comprising compound X (as defined earlier), cystein and/or a hydrogen sulphide donor.

Such flavour precursor mixtures are very useful because the flavour is developed upon heating of the foodstuff to which the precursor mixture is added. Such heating is often done only a few minutes before the foodstuff is ingested so that flavour degeneration and flavour losses are kept to a minimum. However, when aqueous systems are involved lower conversions into flavour compounds may occur and an appropriately higher level of the flavour precursor mixture may be required. The use of such flavour precursor mixtures can also be useful in dry soup mixes and canned meat products, where the flavour is developed upon sterilizing the closed cans. Sometimes it is advantageous to have heated the flavour precursor mixture under mild conditions before incorporating it in a foodstuff; some of the precursor mixture is then already converted into flavour compounds and at the same time the flavour precursor mixture is still present to develop the full flavour at a later stage.

The flavours and flavour precursor mixtures according to the invention may be added to products to be flavoured, either as such, or as part of a flavouring composition. The term flavouring composition as used herein means a mixture of flavours or flavour components, if desired dissolved in a suitable solvent or mixed with a powdered substrate or carrier or processed to form a powdered product. Such a flavouring composition is used to impart a flavour impression to a product or to improve or alter the existing flavour impression of a product.

Thus, in a further embodiment of the invention there is provided a flavouring composition comprising flavours and flavour components known in the art and in addition one or more flavours obtained by the process of the invention and/or flavour precursor mixtures according to the invention.

Examples of products the flavour precursor mixtures according to the invention may be added to, either as such or as part of a flavour composition, are ingredient mixes for products which are prepared by extrusion, frying or baking.

Flavours or flavour components which may be advantageously combined with the flavours or flavour precursor mixtures according to the invention into flavouring compositions are: natural products such as extracts, essential oils, absolutes, resins, concretes, fruit juices, etc., but also synthetic components such as hydrocarbons, alcohols, aldehydes, ketones, esters, ethers, acetals, ketals, acids, etc., including saturated and unsaturated compounds, aliphatic, alicyclic and heterocyclic compounds.

Auxiliary substances and solvents which can be used in flavouring compositions containing the flavours and flavour precursor mixtures according to the invention are, for example: ethanol, isopropanol, diethyleneglycol monoethyl ether, glycerol, triacetin etc. Powdered substrates or carriers may include salt, starch derivatives and the like. Processing into a powdered product may include spray-drying and other techniques of micro-encapsulation.

The savoury flavour mixture of this invention, and/or the flavour precursor mixture, can be used in sauces and stock cubes, for example.

BRIEF DESCRIPTION OF THE DRAWINGS

FIGS. 3a and 3b are gas chromatographs (FID and FPD respectively) of the resultant savory flavor mixture after a reaction time of 1 hour for Comparative Example A.

DETAILED DESCRIPTION OF THE INVENTION

Figure 1A:
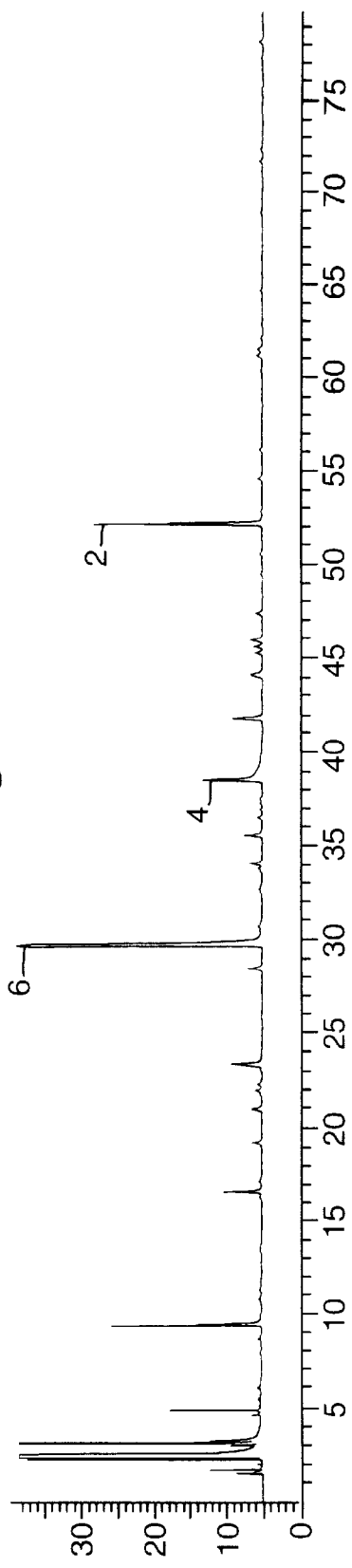
FIGS. 1a and 1b are gas chromatographs (FID and FPD respectively) of the savory flavor mixture after a reaction time of 1 hour for Example 1.

The present invention will now be described, by way of example only, with reference to the accompanying FIGS. 1, 2, 3 and 4.

EXAMPLE 1

104 mmol of 90% 4-hydroxy-2,5-dimethyl-2-(2-hydroxy-3-oxo-2-butyl)-3(2H)-furanone per kg of glycerol and 954 mmol of cysteine per kg of glycerol were added to a 300 ml autoclave.

After closing the autoclave to the atmosphere, the total mixture was stirred and the air/oxygen was removed by flushing with nitrogen after which 644 mmol of hydrogen sulphide gas (15–16 bar) per kg of glycerol was added to the autoclave. The amount of gas added was determined by weighing the gas cylinder. After addition of the hydrogen sulphide, the autoclave was heated to 120° C.

During the reaction, samples of the reaction mixture were taken from the autoclave to determine the formation of flavour compounds.

The samples of reaction mixture were extracted and then analysed by gas chromatography.

Extraction Procedure

Approx 2.7 grams of the crude reaction mixture were diluted with approx 7 grams glycerol, and added to approx 70 ml water. This mixture was extracted by means of a mini Likens Nickerson extraction unit (available from Chrompack) in 2 ml dichloromethane. To prevent foam formation, 3 drops of anti-foaming agent were added to the distillation.

Extraction Conditions

Solvent: 2 ml dichloromethane
Cooling cold finger: −1° C. using a cryostat
Temperature oil bath solvent: 70° C.
Control unit heating mantle: position 3 (140° C.)
Extraction time: 5 mins post 'initial' solvent reflux
  240 mins extraction
  20 mins 'post' solvent reflux To determine quantitatively the amount of flavour compounds formed, $C_{12}$-methylester was added as an internal standard to the dichloromethane extract of the reaction mixture. This internal standard is marked 2 in the relevant figures.

The dichloromethane extract obtained was analysed by gas chromatography using the following conditions:
Gas Chromatograph: Hewlett Packard 5890 series II
Column: CPsil05-CB,1=25 m, i.d.=0.32 mm, df=1.2 μm
$P_{in}$: 8 psi
$T_{injector}$: 240° C.
Detection: FID and FPD (HP accessory 19256A)
$T_{FID}$: 260° C.
$T_{FPD}$: 250° C. (range 2)
oven temperature program: 50° C.—2.5° C./min—250° C.

The column effluent was split to the two detectors using a splitter at the end of the GLC column.

The injector is split and the split ratio is 1:30 ie. 1 part in 30 of the sample enters the column and the rest of the sample is ejected.

Where:

CPsil05-CB is the trade name for a 100% dimethylsiloxane chemically bonded column available from Chrompack.
1: length of column
i.d.: internal diameter of column
df: thickness of the film of the stationary phase in the column
$P_{in}$: inlet pressure
$T_{injector}$: temperature of split/splitless injector
FID: Flame Ionisation Detector
FPD: Flame Photometric detector
$T_{FID}$: Temperature of FID
$T_{FPD}$: Temperature of FPD
HP: Hewlett Packard 50° C.—2.5° C./min—250° C. means that the rate of increase of the temperature of the oven is 2.5° C. per min, starting at a temperature of 50° C. and finishing at a temperature of 250° C.
LTP (Linear Temperature Programme) indices were calculated using an alkanes mix (C5–C20).

The yields of the flavour compounds were calculated on the assumption that their response factor was 1 compared to the internal standard, and that the extraction recovery was 60%.

Figure 1B:
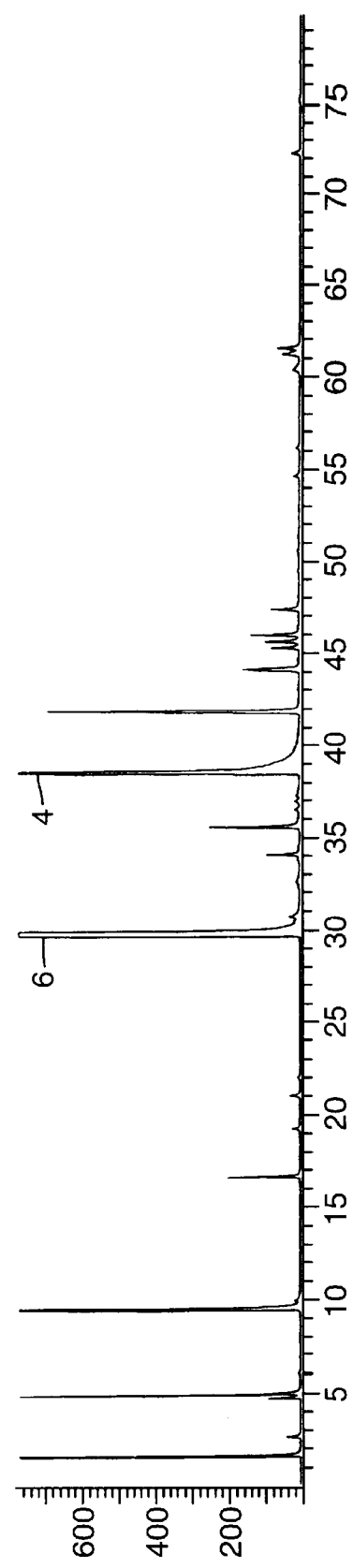

FIGS. 1a and 1b are gas chromatographs (FID and FPD respectively) of the resultant savoury flavour mixture after a reaction time of 1 hour indicating the presence of a number of key flavour compounds, including 2,5-dimethyl-4-mercapto-3(2H)-thiophenone (yield 0.35%) and 2,5-dimethyl-4-mercapto-3(2H)-furanone (yield 4.6%).

After a reaction time of 2 hours, the yields were: 2,5-dimethyl-4-mercapto-3(2H)-thiophenone 6.4% 2,5-dimethyl-4-mercapto-3(2H)-furanone 0.4%

The LTP Index for 2,5-dimethyl-4-mercapto-3(2H)-thiophenone is 1262, and the LTP Index for 2,5-dimethy-4-mercapto-3(2H)-furanone is 1120. Their peaks are marked 4 and 6 respectively in the figures.

COMPARATIVE EXAMPLE A 95 mmol of 95% 4-hydroxy-2,5-dimethyl-3(2H)-furanone per kg of glycerol and 954 mmol of cysteine per kg of glycerol were added to a 300 ml autoclave. The experimental procedure of Example 1 was followed, except that 686 mmol of hydrogen sulphide gas per kg of glycerol was added.

FIGS. 3a and 3b are gas chromatographs (FID & FPD respectively) of the resultant savoury flavour mixture after a reaction time of 1 hour. The yield of 2,5-dimethyl-4-mercapto-3(2H)-furanone (6) after 1 hour was 0.4% (and after 2 hours was 0.2%). The yield of 2,5-dimethyl-4-mercapto-3(2H)-thiophenone (4) after 1 hour was 0% (and after 2 hours was 1.5%).

COMPARATIVE EXAMPLE B 95 mmol of 95% 4-hydroxy-2,5-dimethyl-3(2H)-furanone per kg of glycerol, 100 mmol of diacetyl per kg of glycerol and 954 mmol of cysteine per kg of glycerol were added to a 300 ml autoclave. The experimental procedure of Example 1 was followed, except that 630 mmol of hydrogen sulphide gas per kg of glycerol was added.

Figure 4A:
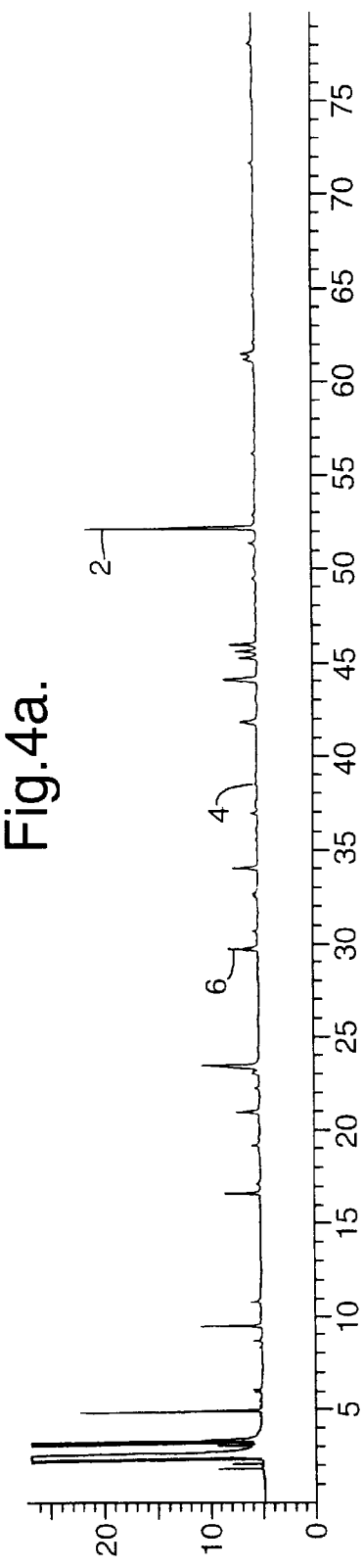
FIGS. 4a and 4b are gas chromatographs (FID and FPD respectively) of the resultant savory flavor mixture after a reaction time of 1 hour for Comparative Example B.
Figure 4B:
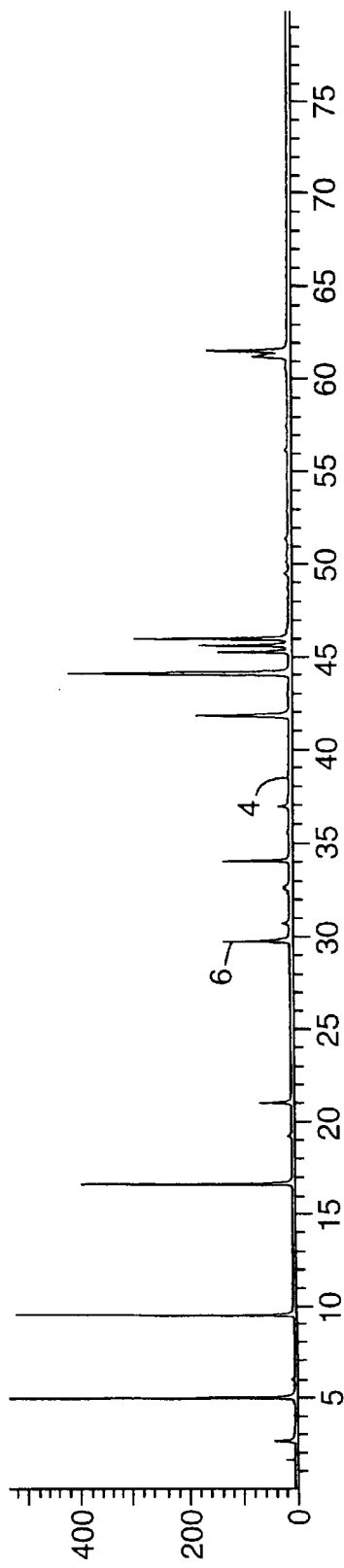

FIGS. 4a and 4b are gas chromatographs (FID & FPD respectively) of the resultant savoury flavour mixture after a reaction time of 1 hour. The yield of 2,5-dimethyl-4-mercapto-3(2H)-furanone (6) was 0.4 after 1 hour (and was 0% after 2 hours). The yield of 2,5-dimethyl-4-mercapto-3(2H)-thiophene (4) was 0% after 1 hour (and 1.3% after 2 hours).

EXAMPLES 2 to 4

COMPARATIVE EXAMPLES C TO H

For examples 2, 3 and 4, the experimental procedure of Example 1 was repeated, but using the component amounts and conditions specified in Table 1.

For comparative example C, the experimental procedure of Example 1 was repeated, but using the component amounts and conditions specified in Table 1 and replacing 4-hydroxy-2,5-dimethyl-2-(2-hydroxy-3-oxo-2-butyl)-3(2H)-furanone with 2,5-dimethyl-3(2H)-furanone. This experiment corresponds to example 9 of EP 571031.

For comparative example D, the experimental procedure of Example 1 was repeated, but using the component amounts and conditions specified in Table 1 and replacing 4-hydroxy-2,5-dimethyl-2-(2-hydroxy-3-oxo-2-butyl)-3(2H)-furanone with 2,5-dimethyl-2-(2-hydroxy-3-oxo-2-butyl)-3(2H)-furanone (the diacetyl oligomer of EP 571031). This experiment corresponds to example 8 of EP 571031.

For examples E, F and G, the experimental procedure of Example 1 was repeated, but using the component amounts and conditions specified in Table 1 and replacing 4-hydroxy-2,5-dimethyl-2-(2-hydroxy-3-oxo-2-butyl)-3(2H)-furanone with 2,5-dimethyl-4-hydroxy-3(2H)-furanone and diacetyl (their adduct 4-hydroxy-2,5-dimethyl-2-(2-hydroxy-3-oxo-2-butyl)-3(2H)-furanone was not formed first so was not present).

For comparative example H, the experimental procedure of Example 1 was repeated, but using the component amounts and conditions specified in Table 1, omitting the addition of cystein and replacing 4-hydroxy-2,5-dimethyl-2-(2-hydroxy-3-oxo-2-butyl)-3 (2H)-furanone with 2,5-dimethyl-4-hydroxy-3(2H)-furanone. This experiment corresponds to example B2 of GB 1283912, although a different ratio of hydrogen sulphide to 2,5-dimethyl-4-hydroxy-3 (2H)-furanone was used.

In example 4 and comparative examples G & H, water was used as a medium instead of glycerol.

The temperatures shown in Table 1 are those to which the autoclave was heated.

During the reactions, samples of the reaction mixture were taken from the autoclave to determine the formation of flavour compounds using gas chromatography, as in example 1.

RESULTS

Table 2 shows the flavour compounds found in samples of reaction mixtures extracted after reaction times of 1 to 4 hours. These compounds, their yields (% and mmol/kg) were analysed by gas chromatography.

Figure 2:
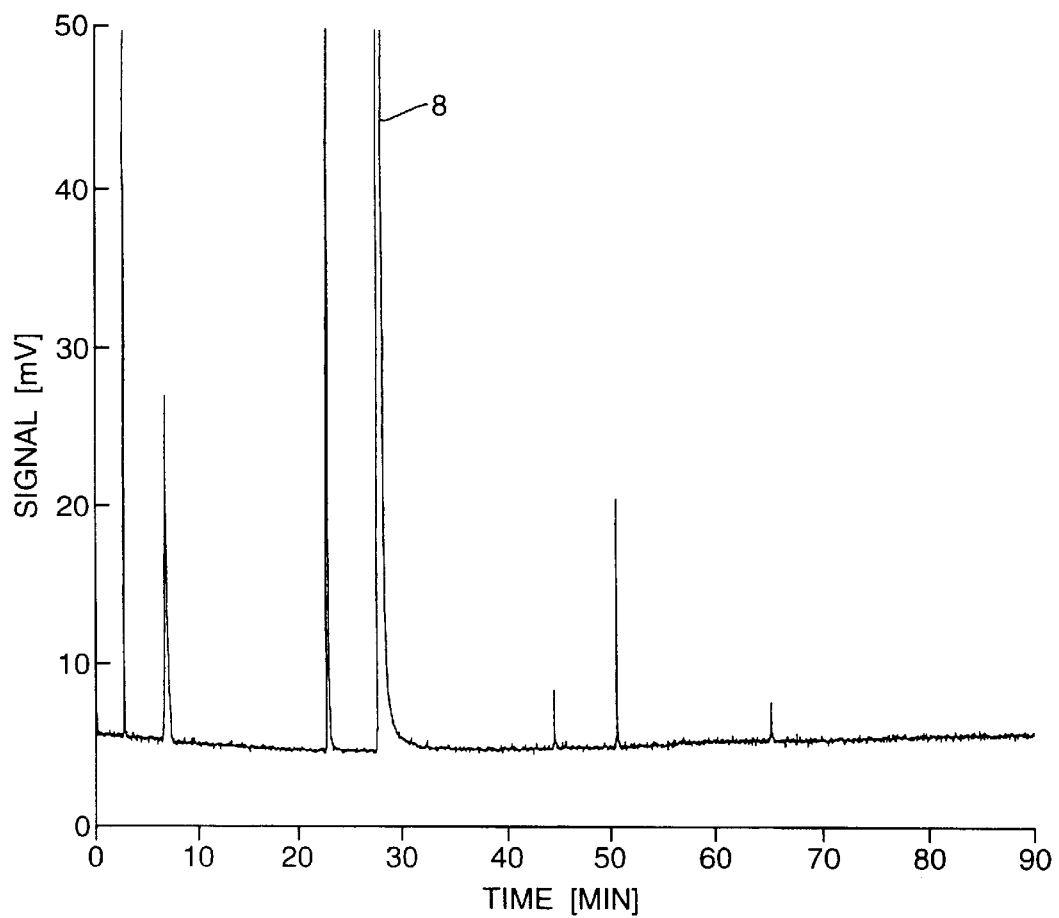
FIG. 2 is a chromatograph of the savory flavor mixture showing that the key sulfur-containing flavor compound (peak 8) is present.

It is evident that comparative examples C and D produced high yields of only one key flavour compound, namely 2,5-dimethylfuranthiol. The gas chromatograph of comparative example D is shown in FIG. 2: peak 8 is 2,5-dimethylfuranthiol.

Comparative example F produced only two key flavour compounds (namely, 2,5-dimethyl-4-mercapto-3(2H)-furanone and 2,5-dimethyl-4-mercapto-3(2H)-thiophenone) and in relatively low amounts.

In comparative examples E, G and H, 2,5-dimethyl-3 (2H)-furanone was present, together with 2,5-dimethyl-4-mercapto-3(2H)-furanone, 2,5-dimethyl-4-mercapto-3(2H)-thiophenone and dihydro 2(4 or 5)-dimethyl-3(2H)-thiophenone (amongst others). However, the yields of these flavour compounds were low.

Experiments 2, 3 and 4 of the present invention provided a wide range of key flavour compounds with particularly good yields of 2,5-dimethyl-4-mercapto-3(2H)-furanone and 2,5-dimethyl-4-mercapto-3(2H)-thiophenone. Experiment 2 provided the best results; from this it can be concluded that the present invention is preferably carried out at 100° C. in glycerol, rather than at 120° C. or in water.

TABLE I

| | mmol/kg | | | | | | | | |
|---|---|---|---|---|---|---|---|---|---|
| example | C | D | E | 2 | 3 | F | G | 4 | H |
| medium | glycerol | glycerol | glycerol | glycerol | glycerol | glycerol | water | water | water |
| temperature (degrees C.) | 120 | 120 | 100 | 100 | 120 | 120 | 100 | 100 | 100 |
| cysteine | 965 | 967 | 968 | 996 | 968 | 990 | 974 | 970 | |
| hydrogensulfide | 428 | 428 | 597 | 581 | 611 | 634 | 429 | 441 | 457 |
| 2,5-dimethyl-3(2H)-furanone | 130 | | | | | | | | |
| diacetyl oligomer | | 125 | | | | | | | |
| 2,5-dimethyl-4-hydroxy-3(2H)-furanone | | | 100 | | | | 101 | | 101 |
| diacetyl | | | 102 | | | | 101 | 102 | |
| fupre2 | | | | | 110 | 100 | | 102 | | fupre2 = 4-hydroxy-2,5-dimethyl-(2-hydroxy-3-oxo-2-butyl)-3(2H)-furanone
diacetyl oligomer = 2,5-dimethyl-2-(2-hydroxy-3-oxo-2-butyl)-3(2H)-furanone
mmol/kg = mmol per kg of medium

TABLE 2

| example | | yield [%] reaction time [hours] | | | | mmol/kg reaction time [hours] | | | |
|---|---|---|---|---|---|---|---|---|---|
| | | 1 | 2 | 3 | 4 | 1 | 2 | 3 | 4 |
| C | 2,5-dimethylfuranthiol | 2.2 | 6.7 | 9.4 | 8.3 | 2.9 | 8.7 | 12.2 | 10.8 |
| D | 2,5-dimethylfuranthiol | 31.7 | 25 | 18.2 | 9.7 | 39.4 | 31.1 | 22.6 | 12.1 |
| E | 2,5-dimethyl-4-mercapto-3(2H)-furanone | 0.03 | 0.40 | 0.62 | 0.42 | 0.03 | 0.40 | 0.63 | 0.42 |
| | 2,5-dimethyl-4-mercapto-3(2H)-thiophenone | 0.00 | 0.00 | 0.03 | 0.04 | 0.00 | 0.00 | 0.00 | 0.00 |
| | 2,5-dimethylfuranthiol | 0.00 | 0.00 | 0.04 | 0.02 | 0.00 | 0.00 | 0.04 | 0.02 |
| | dihydro 2(4 or 5)-dimethyl-3(2H)-thiophenon | 0.08 | 0.20 | 0.34 | 0.52 | 0.08 | 0.20 | 0.34 | 0.52 |
| | 2,5-dimethyl-3(2H)-furanon | 0.06 | 0.09 | 0.10 | 0.13 | 0.06 | 0.09 | 0.10 | 0.13 |
| | 2,5-dimethyl-4-hydroxy-3(2H)-thiophenone | 0.00 | 0.00 | 0.00 | 0.00 | 0.00 | 0.00 | 0.00 | 0.00 |
| | 2,5-dimethyl-3-mercaptothiophene | 0.00 | 0.05 | 0.07 | 0.06 | 0.00 | 0.05 | 0.08 | 0.06 |
| | 2,5-dimethyl-3(2H)-thiophenone | 0.00 | 0.00 | 0.00 | 0.00 | 0.00 | 0.00 | 0.00 | 0.00 |
| 2 | 2,5-dimethyl-4-mercapto-3(2H)-furanone | 7.05 | 10.06 | 8.61 | 8.32 | 7.00 | 10.00 | 8.55 | 8.27 |
| | 2,5-dimethyl-4-mercapto-3(2H)-thiophenone | 0.12 | 0.46 | 0.91 | 1.49 | 0.08 | 0.34 | 0.78 | 1.41 |
| | 2,5-dimethylfuranthiol | 0.03 | 0.09 | 0.11 | 0.16 | 0.03 | 0.09 | 0.11 | 0.16 |
| | dihydro 2(4 or 5)-dimethyl-3(2H)-thiophenon | 0.06 | 0.15 | 0.23 | 0.33 | 0.06 | 0.15 | 0.23 | 0.32 |
| | 2,5-dimethyl-3(2H)-furanon | 0.15 | 0.26 | 0.31 | 0.40 | 0.15 | 0.25 | 0.31 | 0.40 |
| | 2,5-dimethyl-4-hydroxy-3(2H)-thiophenone | 0.02 | 0.04 | 0.06 | 0.07 | 0.02 | 0.04 | 0.06 | 0.07 |
| | 2,5-dimethyl-3-mercaptothiophene | 0.02 | 0.03 | 0.03 | 0.05 | 0.02 | 0.03 | 0.03 | 0.05 |
| | 2,5-dimethyl-3(2H)-thiophenone | 0.00 | 0.01 | 0.03 | 0.05 | 0.00 | 0.01 | 0.03 | 0.05 |
| 3 | 2,5-dimethyl-4-mercapto-3(2H)-thiophenone | 0.41 | 5.04 | n.d | 0.47 | 0.35 | 5.12 | n.d | 0.48 |
| | 2,5-dimethylfuranthiol | 0.05 | 0.28 | n.d | 0.06 | 0.05 | 0.28 | n.d | 0.06 |
| | dihydro 2(4 or 5)-dimethyl-3(2H)-thiophenon | 0.14 | 0.03 | n.d | 0.30 | 0.14 | 0.03 | n.d | 0.3 |
| | 2,5-dimethyl-3(2H)-furanon | 0.18 | 0.35 | n.d | 0.25 | 0.18 | 0.35 | n.d | 0.25 |
| | 2,5-dimethyl-4-hydroxy-3(2H)-thiophenone | 0.01 | 0.13 | n.d | 0.68 | 0.01 | 0.12 | n.d | 0.68 |
| | 2,5-dimethyl-3-mercaptothiophene | 0.02 | 0.29 | n.d | 0.60 | 0.02 | 0.29 | n.d | 0.6 |
| | 2,5-dimethyl-3(2H)-thiophenone | 0.01 | 0.58 | n.d | 1.21 | 0.01 | 0.58 | n.d | 1.21 |
| F | 2,5-dimethyl-4-mercapto-3(2H)-furanone | 0.36 | 0.09 | 0.00 | 0.00 | 0.35 | 0.09 | 0.00 | 0.00 |
| | 2,5-dimethyl-4-mercapto-3(2H)-thiophenone | 0.03 | 1.15 | 1.88 | 0.68 | 0.03 | 1.11 | 1.81 | 0.65 |
| G | 2,5-dimethyl-4-mercapto-3(2H)-furanone | 0.51 | 1.20 | 1.47 | 2.25 | 0.51 | 1.21 | 1.48 | 2.27 |
| | 2,5-dimethyl-4-mercapto-3(2H)-thiophenone | 0.02 | 0.04 | 0.04 | 0.08 | 0.01 | 0.01 | 0.03 | 0.04 |
| | 2,5-dimethylfuranthiol | 0.00 | 0.03 | 0.03 | 0.07 | 0.00 | 0.03 | 0.03 | 0.07 |
| | dihydro 2(4or 5)-dimethyl-3(2H)-thiophenon | 0.03 | 0.06 | 0.10 | 0.13 | 0.03 | 0.06 | 0.10 | 0.13 |
| | 2,5-dimethyl-3(2H)-furanon | 0.02 | 0.06 | 0.13 | 0.21 | 0.02 | 0.06 | 0.13 | 0.22 |
| | 2,5-dimethyl-4-hydroxy-3(2H)-thiophenone | 0.02 | 0.01 | 0.01 | 0.02 | 0.02 | 0.01 | 0.01 | 0.02 |
| | 2,5-dimethyl-3-mercaptothiophene | 0.02 | 0.03 | 0.03 | 0.04 | 0.02 | 0.03 | 0.03 | 0.04 |
| | 2,5-dimethyl-3(2H)-thiophenone | 0.00 | 0.00 | 0.00 | 0.00 | 0.00 | 0.00 | 0.00 | 0.00 |
| 4 | 2,5-dimethyl-4-mercapto-3(2H)-furanone | 3.25 | 3.29 | 3.39 | 3.72 | 3.30 | 3.35 | 3.45 | 3.79 |
| | 2,5-dimethyl-4-mercapto-3(2H)-thiophenone | 0.01 | 0.06 | 0.09 | 0.13 | 0.01 | 0.03 | 0.06 | 0.08 |
| | 2,5-dimethylfuranthiol | 0.00 | 0.02 | 0.05 | 0.10 | 0.00 | 0.02 | 0.05 | 0.11 |
| | dihydro 2(4 or 5)-dimethyl-3(2H)-thiophenon | 0.03 | 0.07 | 0.09 | 0.12 | 0.03 | 0.07 | 0.09 | 0.12 |
| | 2,5-dimethyl-3(2H)-furanon | 0.25 | 0.39 | 0.50 | 0.71 | 0.20 | 0.40 | 0.51 | 0.72 |
| | 2,5-dimethyl-4-hydroxy-3(2H)-thiophenone | 0.00 | 0.00 | 0.01 | 0.02 | 0.00 | 0.00 | 0.01 | 0.02 |
| | 2,5-dimethyl-3-mercaptothiophene | 0.00 | 0.03 | 0.03 | 0.05 | 0.00 | 0.03 | 0.03 | 0.05 |
| | 2,5-dimethyl-3(2H)-thiophenone | 0.00 | 0.00 | 0.00 | 0.00 | 0.00 | 0.00 | 0.00 | 0.00 |
| H | 2,5-dimethyl-4-mercapto-3(2H)-furanone | 0.61 | 1.09 | 1.34 | 1.76 | 0.62 | 1.10 | 1.35 | 1.78 |
| | 2,5-dimethyl-4-mercapto-3(2H)thiophenone | 0.05 | 0.16 | 0.29 | 0.44 | 0.02 | 0.09 | 0.20 | 0.32 |
| | 2,5-dimethylfuranthiol | 0.00 | 0.00 | 0.00 | 0.00 | 0.00 | 0.00 | 0.00 | 0.00 |
| | dihydro 2(4 or 5)-dimethyl-3(2H)-thiophenon | 0.00 | 0.00 | 0.05 | 0.07 | 0.00 | 0.00 | 0.05 | 0.07 |
| | 2,5-dimethyl-3(2H)-furanon | 0.04 | 0.05 | 0.06 | 0.07 | 0.04 | 0.05 | 0.06 | 0.07 |
| | 2,5-dimethyl-4-hydroxy-3(2H)-thiophenone | 0.03 | 0.12 | 0.17 | 0.25 | 0.03 | 0.12 | 0.17 | 0.25 |
| | 2,5-dimethyl-3-mercaptothiophene | 0.00 | 0.00 | 0.00 | 0.00 | 0.00 | 0.00 | 0.00 | 0.00 |
| | 2,5-dimethyl-3(2H)-thiophenone | 0.00 | 0.00 | 0.02 | 0.03 | 0.00 | 0.00 | 0.02 | 0.03 | n.d = not detected
mmol/kg = mmol per kg of medium

EXPERIMENT 5

8.3 g of 4-hydroxy-2,5-dimethyl-3(2H)-furanone, 7.9 g of butanal, 0.2 g of oxalic acid and 19.4 g of water were reacted at room temperature to form an adduct of 4-hydroxy-2,5-dimethyl-3(2H)-furanone and butanal. High Performance Liquid Chromatography was used to confirm the presence of this adduct.

0.5 g of cysteine, 1.0 g diacetyl, 49.3 g glycerol and 1.9 g of water were added to 11.5 g of the adduct and heated in an open system at 100° C. for one hour. The reaction products were isolated by Likens Nickerson distillation and analysed by Gas Liquid Chromatography, as in example 1.

EXPERIMENT 6

7.3 g of 4-hydroxy-2,5-dimethyl-3(2H)-furanone, 6.9 g of 2,3-pentanedione, 0.2 g of oxalic acid and 20.3 g of water were reacted at room temperature to form an adduct of 4-hydroxy-2,5-dimethyl-3(2H)-furanone and 2,3-pentanedione. High Performance Liquid Chromatography was used to confirm the presence of this adduct.

0.5 g of cysteine, 1.0 g diacetyl, 49.3 g glycerol and 1.9 g of water were added to 4.3 g of the adduct and heated in an open system at 100° C. for one hour. The reaction products were isolated by Likens Nickerson distillation and analysed by Gas Liquid Chromatography, as in example 1.

COMPARATIVE EXAMPLE I 8.0 g of 4-hydroxy-2,5-dimethyl-3(2H)-furanone, 0.5 g of cysteine, 1.0 g of diacetyl, 49.3 g of glycerol and 1.9 g of water were heated together in an open system at 100° C. for one hour. The reaction products were isolated by Likens Nickerson distillation and analysed by Gas Liquid Chromatography, as in example 1.

RESULTS

The yields of 2,5-dimethyl-4-mercapto-3(2H)-furanone were as follows:
example 5=0.2%
example 6=0.3%
comparative example I=0.02%.

FLAVOUR DESCRIPTION 2,5-dimethyl-4-mercapto-3(2H)-furanone is sweet, onion-like, meaty, full flavour.

SUMMARY

In closed systems, the experiments of Examples 1 to 4 resulted in better yields of certain key flavour compounds (particularly 2,5-dimethyl-4-mercapto-3(2H)-furanone) than the experiments of Comparative Examples A to H.

In open systems, the experiments of Example 5 and 6 also resulted in better yields of 2,5-dimethyl-4-mercapto-3(2H)-furanone than the experiment of Comparative Example I. However, the yields of this flavour compound were considerably lower using an open system rather than a closed system.

We claim:

1. A process for the preparation of a savoury flavour, the process comprising reacting a compound of general formula X with at least one compound selected from the group consisting of hydrogen sulphide, cystein, and mixtures thereof wherein X is:

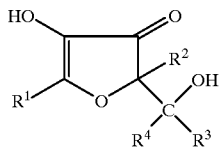

in which $R^1$ represents an alkyl group having 1 or 2 carbon atoms or hydrogen, $R^2$ represents an alkyl group having from 1 to 4 carbon atoms or hydrogen, $R^3$ represents an alkyl group having from 1 to 5 carbon atoms or hydrogen and $R^4$ represents hydrogen or an organic radical consisting of from 1 to 6 carbon atoms, hydrogen and from 0 to 2 oxygen atoms.

2. A process as claimed in claim 1 wherein the sum of the number of carbon atoms of $R^3$ and the number of carbon atoms of $R^4$ is less than or equal to seven.

3. A process as claimed in claim 1 wherein when $R^3$ represents a methyl or ethyl group, $R^4$ contains no more than four carbon atoms.

4. A process as claimed in claim 1, further comprising the step of forming compound X, the step comprising reacting a compound of general formula Y with a compound of general formula Z, where Y is:

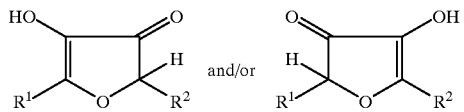

and Z is:

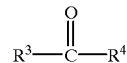

5. A process as claimed in claim 4, wherein compound Z is selected from the group consisting of diacetyl, butanal, hexanal, pyruvic aldehyde, pyruvic acid, acetoin, acetol, ethylene glycol aldehyde, pentanedione, glyceraldehyde and is mixtures thereof.

6. A process as claimed in claim 4, wherein compound Y is selected from the group consisting of 4-hydroxy-2,5-dimethyl-3(2H)-furanone, 4-hydroxy-2-methyl-3(2H)-furanone, 4-hydroxy-5-methyl-3(2H)-furanone, 3-hydroxy-2,5-dimethyl-4(5H)-furanone, 3-hydroxy-2-methyl-4-(5H)-furanone, 3-hydroxy-5-methyl-4(5H)-furanone and mixtures thereof.

7. A process as claimed in claim 1 wherein compound X is selected from the group consisting of 4-hydroxy-2,5-dimethyl-2-(2-hydroxy-3-oxo-2-butyl)-3(2H)-furanone, 4-hydroxy-2-methyl-2-(2-hydroxy-3-oxo-2-butyl)-3(2H)-furanone, 4-hydroxy-5-methyl-2-(2-hydroxy-3-oxo-2-butyl)-3(2H)-furanone and mixtures thereof.

8. A process as claimed in claim 1, wherein the molar ratio of compound X: cystein: hydrogen sulphide is within the range 1:5–15:0–10.

9. A process as claimed in claim 8, wherein the molar range of compound X: cystein: hydrogen sulphide is within the range 1:7–9:3–5.

10. A process as claimed in claim 1, wherein 2,5-dimethyl-4-mercapto-3(2H)-furanone is prepared.

* * * * *